(12) United States Patent
Cramer

(10) Patent No.: US 11,357,598 B2
(45) Date of Patent: Jun. 14, 2022

(54) DENTAL ARCH ANALYSIS AND TOOTH NUMBERING

(71) Applicant: Align Technology, Inc., San Jose, CA (US)

(72) Inventor: Christopher E. Cramer, Durham, NC (US)

(73) Assignee: Align Technology, Inc., San Jose, CA (US)

( * ) Notice: Subject to any disclaimer, the term of this patent is extended or adjusted under 35 U.S.C. 154(b) by 81 days.

(21) Appl. No.: 16/839,063

(22) Filed: Apr. 2, 2020

(65) Prior Publication Data

US 2020/0315744 A1 Oct. 8, 2020

Related U.S. Application Data

(60) Provisional application No. 62/828,956, filed on Apr. 3, 2019.

(51) Int. Cl.
*A61C 7/00* (2006.01)
*A61C 9/00* (2006.01)

(52) U.S. Cl.
CPC ............ *A61C 7/002* (2013.01); *A61C 9/0053* (2013.01); *A61C 2007/004* (2013.01)

(58) Field of Classification Search
CPC .. A61C 7/002; A61C 9/0053; A61C 2007/004
See application file for complete search history.

(56) References Cited

U.S. PATENT DOCUMENTS

| | | |
|---|---|---|
| 5,975,893 A | 11/1999 | Chishti et al. |
| 6,227,850 B1 | 5/2001 | Chishti et al. |
| 6,227,851 B1 | 5/2001 | Chishti et al. |
| 6,299,440 B1 | 10/2001 | Phan et al. |
| 6,318,994 B1 | 11/2001 | Chishti et al. |
| 6,371,761 B1 | 4/2002 | Cheang et al. |
| 6,386,878 B1 | 5/2002 | Pavlovskaia et al. |
| 6,406,292 B1 | 6/2002 | Chishti et al. |
| 6,409,504 B1 | 6/2002 | Jones et al. |
| 6,457,972 B1 | 10/2002 | Chishti et al. |
| 6,488,499 B1 | 12/2002 | Miller |
| 6,514,074 B1 | 2/2003 | Chishti et al. |
| 6,582,229 B1 | 6/2003 | Miller et al. |
| 6,602,070 B2 | 8/2003 | Miller et al. |
| 6,621,491 B1 | 9/2003 | Baumrind et al. |
| 6,688,886 B2 | 2/2004 | Hughes et al. |
| 6,726,478 B1 | 4/2004 | Isiderio et al. |
| 6,729,876 B2 | 5/2004 | Chishti et al. |
| 6,739,869 B1 | 5/2004 | Taub et al. |
| 6,767,208 B2 | 7/2004 | Kaza |
| 6,783,360 B2 | 8/2004 | Chishti |
| 7,040,896 B2 | 5/2006 | Pavlovskaia et al. |
| 7,063,532 B1 | 6/2006 | Jones et al. |

(Continued)

FOREIGN PATENT DOCUMENTS

WO 9858596 A1 12/1998

*Primary Examiner* — Nicholas D Lucchesi
(74) *Attorney, Agent, or Firm* — Shay Glenn LLP

(57) ABSTRACT

Provided herein are methods and apparatuses for analyzing a patient's dental arches in order to generate a treatment plan for the dentition. In particular described herein are methods and apparatuses for determining accurate standardized tooth numbering even when there are missing and/or supernumerary teeth.

27 Claims, 7 Drawing Sheets

(56) References Cited

U.S. PATENT DOCUMENTS

| | | |
|---|---|---|
| 7,074,038 B1 | 7/2006 | Miller |
| 7,074,039 B2 | 7/2006 | Kopelman et al. |
| 7,077,647 B2 | 7/2006 | Choi et al. |
| 7,108,508 B2 | 9/2006 | Hedge et al. |
| 7,134,874 B2 | 11/2006 | Chishti et al. |
| 7,156,661 B2 | 1/2007 | Choi et al. |
| 7,160,107 B2 | 1/2007 | Kopelman et al. |
| 7,241,142 B2 | 7/2007 | Abolfathi et al. |
| 7,293,988 B2 | 11/2007 | Wen |
| 7,309,230 B2 | 12/2007 | Wen |
| 7,357,634 B2 | 4/2008 | Knopp |
| 7,555,403 B2 | 6/2009 | Kopelman et al. |
| 7,637,740 B2 | 12/2009 | Knopp |
| 7,689,398 B2 | 3/2010 | Cheng et al. |
| 7,736,147 B2 | 6/2010 | Kaza et al. |
| 7,746,339 B2 | 6/2010 | Matov et al. |
| 7,844,356 B2 | 11/2010 | Matov et al. |
| 7,844,429 B2 | 11/2010 | Matov et al. |
| 7,865,259 B2 | 1/2011 | Kuo et al. |
| 7,878,804 B2 | 2/2011 | Korytov et al. |
| 7,880,751 B2 | 2/2011 | Kuo et al. |
| 7,904,308 B2 | 3/2011 | Arnone et al. |
| 7,930,189 B2 | 4/2011 | Kuo |
| 7,942,672 B2 | 5/2011 | Kuo |
| 7,970,627 B2 | 6/2011 | Kuo et al. |
| 7,970,628 B2 | 6/2011 | Kuo et al. |
| 8,038,444 B2 | 10/2011 | Kitching et al. |
| 8,044,954 B2 | 10/2011 | Kitching et al. |
| 8,075,306 B2 | 12/2011 | Kitching et al. |
| 8,092,215 B2 | 1/2012 | Stone-Collonge et al. |
| 8,099,268 B2 | 1/2012 | Kitching et al. |
| 8,108,189 B2 | 1/2012 | Chelnokov et al. |
| 8,126,726 B2 | 2/2012 | Matov et al. |
| 8,260,591 B2 | 9/2012 | Kass et al. |
| 8,275,180 B2 | 9/2012 | Kuo |
| 8,401,826 B2 | 3/2013 | Cheng et al. |
| 8,439,672 B2 | 5/2013 | Matov et al. |
| 8,562,338 B2 | 10/2013 | Kitching et al. |
| 8,591,225 B2 | 11/2013 | Wu et al. |
| 8,788,285 B2 | 7/2014 | Kuo |
| 8,843,381 B2 | 9/2014 | Kuo et al. |
| 8,874,452 B2 | 10/2014 | Kuo |
| 8,896,592 B2 | 11/2014 | Boltunov et al. |
| 8,930,219 B2 | 1/2015 | Trosien et al. |
| 9,037,439 B2 | 5/2015 | Kuo et al. |
| 9,060,829 B2 | 6/2015 | Sterental et al. |
| 9,125,709 B2 | 9/2015 | Matty |
| 9,211,166 B2 | 12/2015 | Kuo et al. |
| 9,220,580 B2 | 12/2015 | Borovinskih et al. |
| 9,364,296 B2 | 6/2016 | Kuo |
| 9,375,300 B2 | 6/2016 | Matov et al. |
| 9,414,897 B2 | 8/2016 | Wu et al. |
| 9,492,245 B2 | 11/2016 | Sherwood et al. |
| 9,642,678 B2 | 5/2017 | Kuo |
| 10,248,883 B2 | 4/2019 | Borovinskih et al. |
| 10,342,638 B2 | 7/2019 | Kitching et al. |
| 10,463,452 B2 | 11/2019 | Matov et al. |
| 10,595,966 B2 | 3/2020 | Carrier, Jr. et al. |
| 10,617,489 B2 | 4/2020 | Grove et al. |
| 10,722,328 B2 | 7/2020 | Velazquez et al. |
| 10,758,322 B2 | 9/2020 | Pokotilov et al. |
| 10,779,718 B2 | 9/2020 | Meyer et al. |
| 10,792,127 B2 | 10/2020 | Kopelman et al. |
| 10,828,130 B2 | 11/2020 | Pokotilov et al. |
| 10,835,349 B2 | 11/2020 | Cramer et al. |
| 10,973,611 B2 | 4/2021 | Pokotilov et al. |
| 10,996,813 B2 | 5/2021 | Makarenkova et al. |
| 10,997,727 B2 | 5/2021 | Xue et al. |
| 2003/0008259 A1 | 1/2003 | Kuo et al. |
| 2003/0143509 A1 | 7/2003 | Kopelman et al. |
| 2003/0207227 A1 | 11/2003 | Abolfathi |
| 2004/0137400 A1 | 7/2004 | Chishti et al. |
| 2004/0152036 A1 | 8/2004 | Abolfathi |
| 2004/0197728 A1 | 10/2004 | Abolfathi et al. |
| 2004/0259049 A1 | 12/2004 | Kopelman et al. |
| 2005/0182654 A1 | 8/2005 | Abolfathi et al. |
| 2005/0244791 A1 | 11/2005 | Davis et al. |
| 2006/0127836 A1 | 6/2006 | Wen |
| 2006/0127852 A1 | 6/2006 | Wen |
| 2006/0127854 A1 | 6/2006 | Wen |
| 2006/0275731 A1 | 12/2006 | Wen et al. |
| 2006/0275736 A1 | 12/2006 | Wen et al. |
| 2008/0306724 A1 | 12/2008 | Kitching et al. |
| 2009/0246726 A1* | 10/2009 | Chelnokov ........ A61C 13/0004 433/24 |
| 2010/0009308 A1 | 1/2010 | Wen et al. |
| 2010/0068672 A1 | 3/2010 | Arjomand et al. |
| 2010/0068676 A1 | 3/2010 | Mason et al. |
| 2010/0092907 A1 | 4/2010 | Knopp |
| 2010/0167243 A1 | 7/2010 | Spiridonov et al. |
| 2013/0204599 A1 | 8/2013 | Matov et al. |
| 2016/0135925 A1 | 5/2016 | Mason et al. |
| 2016/0242870 A1 | 8/2016 | Matov et al. |
| 2016/0310235 A1 | 10/2016 | Derakhshan et al. |
| 2017/0169562 A1* | 6/2017 | Somasundaram .... G06T 7/0012 |
| 2017/0273760 A1 | 9/2017 | Morton et al. |
| 2018/0168775 A1 | 6/2018 | Derakhshan et al. |
| 2018/0280118 A1 | 10/2018 | Cramer |
| 2019/0029784 A1 | 1/2019 | Moalem et al. |
| 2019/0053876 A1 | 2/2019 | Sterental et al. |
| 2019/0076214 A1 | 3/2019 | Nyukhtikov et al. |
| 2019/0105127 A1 | 4/2019 | Velazquez et al. |
| 2019/0175303 A1 | 6/2019 | Akopov et al. |
| 2019/0192259 A1 | 6/2019 | Kopelman et al. |
| 2019/0328487 A1 | 10/2019 | Levin et al. |
| 2019/0328488 A1 | 10/2019 | Levin et al. |
| 2019/0333622 A1 | 10/2019 | Levin et al. |
| 2019/0343601 A1 | 11/2019 | Roschin et al. |
| 2019/0350680 A1 | 11/2019 | Chekh et al. |
| 2019/0357997 A1 | 11/2019 | Shi et al. |
| 2020/0000551 A1 | 1/2020 | Li et al. |
| 2020/0000552 A1 | 1/2020 | Mednikov et al. |
| 2020/0000554 A1 | 1/2020 | Makarenkova et al. |
| 2020/0000555 A1 | 1/2020 | Yuryev et al. |
| 2020/0015943 A1* | 1/2020 | Reynard ................ G16H 40/63 |
| 2020/0085546 A1 | 3/2020 | Li et al. |
| 2020/0105028 A1 | 4/2020 | Gao et al. |
| 2020/0107915 A1 | 4/2020 | Roschin et al. |
| 2020/0146646 A1* | 5/2020 | Tuzoff .................. G06T 7/0012 |
| 2020/0155274 A1 | 5/2020 | Pimenov et al. |
| 2020/0214800 A1 | 7/2020 | Matov et al. |
| 2020/0297458 A1 | 9/2020 | Roschin et al. |
| 2020/0306011 A1 | 10/2020 | Chekhonin et al. |
| 2020/0306012 A1 | 10/2020 | Roschin et al. |
| 2020/0360109 A1 | 11/2020 | Gao et al. |
| 2021/0073998 A1 | 3/2021 | Brown et al. |
| 2021/0074011 A1* | 3/2021 | Cheng ...................... G06T 7/73 |

* cited by examiner

```
Algorithm 1 Tree-Based Maximum Likelihood Solver
 1: function SOLVE(P, λ_s)
 2:     Global  LP ← log[P]
 3:     Global  LP2
 4:     Global  best ← -∞
 5:     Global  Best S̄ ← []
 6:     Global  Best M̄ ← []
 7:     N_o ← rows(P)
 8:     N_c ← 16
 9:     M_s ← N_o
10:     for s ← 0, ..., N_o do
11:         candidate ← array of length (N_o - s)
12:         S(N_o - s, 0, 0, log Poisson(s, λ_s), s, candidate)
13: function S(TreeDepth, level, initial, LogLikelihood, SupernumeraryLeft, candidate)
14:     if level = TreeDepth then                                                            ▷ leaf node
15:         for i ← 0, ..., SupernumeraryLeft - 1 do                      ▷ account for remaining supernumeraries
16:             LogLikelihood ← LogLikelihood + LP_{level+i, N_c}
17:         if LogLikelihood > best then
18:             LP2 ← LP[candidate]                                              ▷ get non-supernumerary rows
19:             candidateM ← array of length TreeDepth
20:             M(TreeDepth, 0, 0, LogLikelihood, N_o - TreeDepth, candidateM, candidate)
21:         return
22:     if LogLikelihood < best then                                                         ▷ prune
23:         return
24:     for i ← 0, ..., SupernumeraryLeft do
25:         if i > 0 then                                                    ▷ add in supernumerary log probability
26:             LogLikelihood ← LogLikelihood + LP_{initial+i-1, N_c}
27:         candidate[level] ← initial + i
28:         S(TreeDepth, level + 1, initial + i + 1, LogLikelihood, SupernumeraryLeft - i, candidate)
29: function M(TreeDepth, level, initial, LogLikelihood, MissingLeft, candidate, candidateS)
30:     if level = TreeDepth then                                                            ▷ leaf node
31:         if LogLikelihood > best then
32:             best ← LogLikelihood
33:             Best S̄ ← candidateS
34:             Best M̄ ← candidate
35:         return
36:     if LogLikelihood < best then                                                         ▷ prune
37:         return
38:     for i ← 0, ..., MissingLeft do
39:         candidate[level] ← initial + i
40:         LogLikelihood' ← LogLikelihood + LP2_{level, initial+i}
41:         M(TreeDepth, level + 1, initial + i + 1, LogLikelihood', MissingLeft - i, candidate, candidateS)
```

FIG. 5

DENTAL ARCH ANALYSIS AND TOOTH NUMBERING

CLAIM OF PRIORITY

This patent application claims priority to U.S. Provisional Patent Application No. 62/828,956, filed Apr. 3, 2019 and titled "DENTAL ARCH ANALYSIS AND TOOTH NUMBERING," which is herein incorporated by reference in its entirety.

INCORPORATION BY REFERENCE

All publications and patent applications mentioned in this specification are incorporated herein by reference in their entirety to the same extent as if each individual publication or patent application was specifically and individually indicated to be incorporated by reference.

BACKGROUND

Orthodontic or dental treatment plans may improve both the function and aesthetics of a patient's teeth. Many treatment plans involve correcting the patient's dentition, which generally pertains to the development and arrangement of teeth. Treatment plans typically address misalignment of teeth within a dental arch or between the dental arches. Creating a treatment plan may be highly complex. Thus, users (e.g., dental practitioners including dentists, orthodontists, dental technicians, etc.) may rely on imaging tools to characterized the patient's dentition. Such tools may help with both the analysis of the patient's existing dentition and/or may provide insights to guide improvements in the dentition and the effect of possible treatments. For instance, an optical scan of a patient's arches may be used to represent teeth in the arches using three-dimensional (3D) dental mesh models. Such 3D dental mesh models may help practitioners visualize teeth arrangements and/or simulate treatment outcomes. Many digital scan technologies use automated tooth segmentation systems that identify and/or number individual teeth and/or dental features in a 3D dental mesh model.

Despite these tools, it may be difficult to accurately characterize the patient's dentition. This is partially because dentitions may vary widely from patient to patient. For example, some patients have missing teeth, supernumerary teeth or abnormally formed teeth. Such variations may have any of a number of causes, such as loss or damage of a tooth through trauma or activities, genetic variation, prior extraction, or development disturbances. These variations can cause the dental scanning systems to misidentify and misnumber the teeth. For instance, missing teeth may be misidentified or missed entirely by automated tooth segmentation systems and/or conventional digital scanning technologies, and supernumerary teeth may be misidentified as regular teeth. Tools that more accurately take into account variations in dentitions would be helpful in creating effective treatment plans.

SUMMARY OF THE DISCLOSURE

Described herein are methods and apparatuses (e.g., devices and systems, including computer-implemented instructions) for assisting a user, such as a dentist, orthodontist, or dental technician, in preparing a treatment plan to improve a patient's dentition. Any of these methods and apparatuses may address one or more needs to accurately identify teeth in computer models for orthodontic diagnostics and treatment. For example, any of these methods and apparatuses may be configured to automatically identify dental structures of a patient's dental arches and accurately number the teeth within the arches according to tooth type (e.g., incisor, canine, premolar, molar, etc.). The resulting metric may aid the user in interpreting the patient's dentition and/or in designing one or more treatment plans for improving the patient's dentition.

In one aspect, the analysis may use as input a previously generated probability distribution of numbered teeth in a dental arch. For example, the probability distribution may be in the form of a matrix that includes probabilities of objects observed in the dental arch (e.g., from scanning) corresponding to tooth numbers. Results of the analysis may be used to modify the probability distribution to more accurately reflect the proper numbering of the teeth within the dental arch. In some cases, the teeth can be re-numbered properly to account for one or more supernumerary teeth, one or more missing teeth and/or one or more oddly shaped teeth.

In one aspect, an example of a method (e.g., a computer-implemented method) for accurately assigning tooth numbering to teeth of a patient's dental arch, the method comprising: receiving or identifying tooth objects from a digital model of the patient's dental arch; determining a set of probabilities including, for each identified tooth object from the digital model of the patient's dental arch, a probability that the tooth object corresponds to each possible tooth type, wherein each possible tooth type includes a set of known teeth types and one or more supernumerary teeth; and assigning a tooth numbering to each tooth object from the digital model of the patient's dental arch based on determining a maximum joint probability distribution for each of the identified tooth objects using the set of probabilities.

For example a method (e.g., a computer-implemented method) for accurately assigning tooth number to teeth of a patient's dental arch may include: receiving or identifying tooth objects (and in any of these method, receiving of identifying tooth location) from a digital model of the patient's dental arch; determining a set of probabilities including, for each identified tooth object from the digital model of the patient's dental arch, a probability that the tooth object corresponds to each possible tooth type, wherein each possible tooth type includes a set of known teeth types and one or more supernumerary teeth; and assigning a tooth numbering to each tooth object from the digital model of the patient's dental arch based on determining a maximum joint probability over a distribution of each possible tooth type for each of the identified tooth objects using the set of probabilities.

In any of these methods and apparatuses for performing them, determining the set of probabilities may include a probability of missing teeth. The probability of missing teeth may be assumed to be equally likely for each tooth type. In some variations, the probability of missing teeth may instead be based on one or more of: a gap distance between the teeth, and predetermined value based on tooth type. For example, the probability of a missing tooth may be based on a set of pre-determined (e.g., empirically determined) values based on the tooth type and/or location and/or patient age, etc. The probability of a missing tooth may be incorporated into the probability that a particular tooth corresponds to each possible tooth type.

Receiving or identifying tooth objects may comprise identifying tooth objects from the digital model of the patient's dental arch by segmenting the digital model of the patient's dental arch. Receiving or identifying tooth objects may comprise receiving the digital model of the patient's dental arch with the tooth objects identified.

Determining a maximum of a joint probability distribution for all identified tooth objects may comprise traversing a branched multitree structures having one tree for each of the one or more supernumerary teeth assignments, wherein each leaf node of each tree is a subset of possible tooth numbering assignments for the identified tooth objects and each internal node is a partial probability that represents the probability of a subset of a potential solution. For example, the trees may be traversed so as to find the maximum of a joint probability distribution by starting with an initial best probability value, for example 0, and eliminating branches of the tree having a lower joint probability than a current best assignment probability, wherein the current best assignment probability is based on the total assignment probability of teeth having a higher probability than the previous best assignment probability.

The known teeth types may be standard tooth numbers, e.g., 1-16, 1-32, etc. for any standard tooth numbering system, or for an arbitrary tooth numbering system. For example, the known teeth types may be represented using one or more of: Universal Numbering System (1-32), Palmer Notation, and ISO 3950 FDI World Dental Federation notation. Each possible tooth type may include a set of known teeth types and any number of supernumerary teeth (e.g., at least two supernumerary teeth). In general, the tooth objects may be missing at least one tooth object corresponding to a standard tooth number.

Any of these methods may include creating an orthodontic treatment plan to reposition at least one tooth of the patient using the assigned tooth numbering. Determining the set of probabilities may comprise determining an initial set of probabilities using any 2D or 3D approach for generating probabilities, such as principal components analysis, spherical harmonics analysis, convolutional networks in 2D or 3D, or graph-based networking based on 3d meshes.

For example a computer-implemented method for accurately assigning tooth numbering to teeth of a patient's dental arch may include: receiving or identifying tooth objects from a digital model of the patient's dental arch; determining a set of probabilities including, for each identified tooth object from the digital model of the patient's dental arch, a probability that the tooth object corresponds to each possible tooth type, wherein each possible tooth type includes a set of known teeth types and one or more supernumerary teeth; determining the maximum of a joint probability distribution for each of the identified tooth objects using the set of probabilities by traversing one or more a branched structures having nodes between each branch wherein each node is a subset of possible tooth numbering assignments for the identified tooth objects; and assigning a tooth numbering to each tooth object from the digital model of the patient's dental arch based on the maximum of the joint probability distribution for each of the identified tooth objects.

Also described herein are systems for performing any of the methods described herein. For example a system may include: one or more processors; a memory coupled to the one or more processors, the memory configured to store computer-program instructions, that, when executed by the one or more processors, perform a computer-implemented method comprising: receiving or identifying tooth objects from a digital model of the patient's dental arch; determining a set of probabilities including, for each identified tooth object from the digital model of the patient's dental arch, a probability that the tooth object corresponds to each possible tooth type, wherein each possible tooth type includes a set of known teeth types and one or more supernumerary teeth; and assigning a tooth numbering to each tooth object from the digital model of the patient's dental arch based on determining a maximum joint probability distribution for each of the identified tooth objects using the set of probabilities.

Any of the methods described herein may be implemented as software, firmware and/or hardware. For example, any of the method described herein may be formed as software on a non-transitory computer-readable medium. In some variations, described herein are non-transitory computer-readable medium including contents (e.g., instructions, such as software) that are configured to cause one or more processors to perform a method comprising: receiving or identifying tooth objects from a digital model of the patient's dental arch; determining a set of probabilities including, for each identified tooth object from the digital model of the patient's dental arch, a probability that the tooth object corresponds to each possible tooth type, wherein each possible tooth type includes a set of known teeth types and one or more supernumerary teeth; and assigning a tooth numbering to each tooth object from the digital model of the patient's dental arch based on determining a maximum joint probability over a distribution of each possible tooth type for each of the identified tooth objects using the set of probabilities.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 5 is one example of a method (shown as an algorithmic description) for a tree-based maximum likelihood solver.

DETAILED DESCRIPTION

Figure 1A:
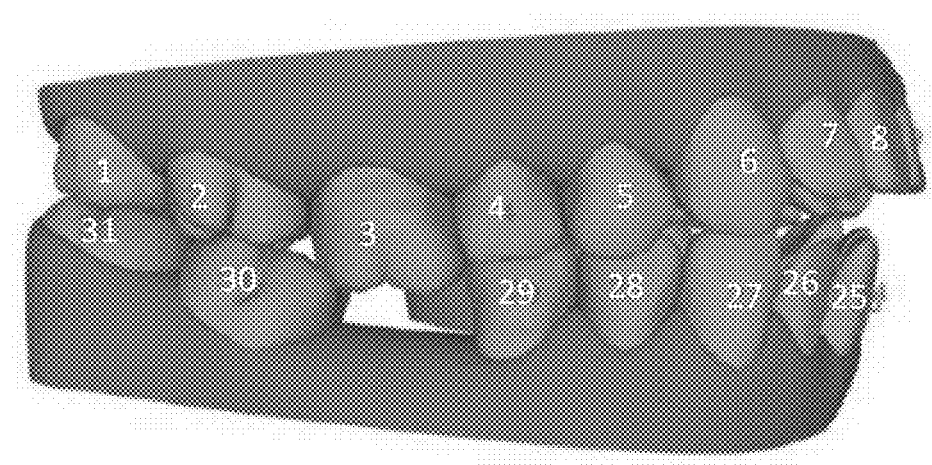
FIGS. 1A-1B illustrate a 3D model of a patient's teeth improperly and properly numbered, respectively, due to a missing tooth.

The present disclosure is related to systems, methods, computing device readable media, and devices for applying an analysis on an estimated dental notation derived from one or more scans of a patent's dentition. The scan may be a two-dimensional (2D) scan, a three-dimensional (3D) scan, or both. In some cases, the data is derived from one or more 2D or 3D modeling techniques. The analysis may account for variations in the dentition that the modeling technique(s) may not be able to accurately resolve. The variations may include supernumerary teeth, missing teeth, abnormally shaped teeth, or any combination thereof. The results of the analysis can be used to characterize the types of teeth in patent's dentition, for example, by providing a corresponding dental notation. In some cases, the information may be used to form dental appliances.

The planning and fabrication of such dental appliances, including elastic polymeric positioning appliances, is described in detail in U.S. Pat. No. 5,975,893, and in published PCT application WO 98/58596, which is herein incorporated by reference for all purposes. Systems of dental appliances employing technology described in U.S. Pat. No. 5,975,893 are commercially available from Align Technology, Inc., San Jose, Calif., under the tradename, Invisalign® System. Throughout the instant paper, the use of the terms "orthodontic aligner", "aligner", or "dental aligner" is synonymous with the use of the terms "appliance" and "dental appliance" in terms of dental applications. For purposes of clarity, embodiments are hereinafter described within the context of the use and application of appliances, and more specifically "dental appliances."

The methods described herein can be used to characterize a patient's dentition and diagnose any malpositioned teeth in the dentition. In some instance, the methods are integrated into an orthodontic treatment plan. For example, the methods can be used to determine positions of the patient's teeth during implementation of the treatment plan (e.g., between treatments) to determine whether the treatments are working as expected. Characterization of the patient's dentition may be made automatically (e.g., using a computing device). For example, the characterization can be performed by a computing system automatically by evaluating data (such as a scan or dental impression) of the patient's teeth or arches.

As described herein, any of a variety of tools can be used to convert a "real world" representation of a patient's dentition into a virtual model. For example, an image (e.g., picture or scan) of the dentition can be converted to a 2D or 3D model (e.g., 2D or 3D mesh). Such tools can include various commercially available products from Align Technology, Inc. In some cases, a number of images are combined to create a single model. In some examples, an intraoral scanner generates multiple different images of a dental site, model of a dental site, or other object. The images may be discrete images (e.g., point-and-shoot images) or frames from a video (e.g., a continuous scan). The intraoral scanner may automatically generate a 3D model of the patient's teeth. In some cases, the 3D model includes the digital detailing and cut and detail processes during which a 3D mesh is converted into a CAD model with labeled teeth. Examples of 2D image conversion products may include Invisalign® SmileView™, Inc. provided by Align Technology, Inc.

In a number of systems, a digital representation of a dental arch is partition into constituent parts, including teeth. This process is sometimes referred to segmentation or auto-segmentation. The teeth are then identified and numbered according to their dental tooth type. The tooth numbering may be used to create a treatment plan for correcting teeth locations. The process for both 2D images and 3D meshes generally begins by identifying which objects in the representation correspond to the central incisors and then working distally to identify the tooth number corresponding to the other objects. This process may cause errors in numbering if there are missing teeth and/or supernumerary teeth. For example, if a patient is missing their first premolars, then the system may mislabel the second premolars as first premolars and the first molars as second premolars. This is particularly likely when the patient's teeth differ from the norm.

Figure 1B:
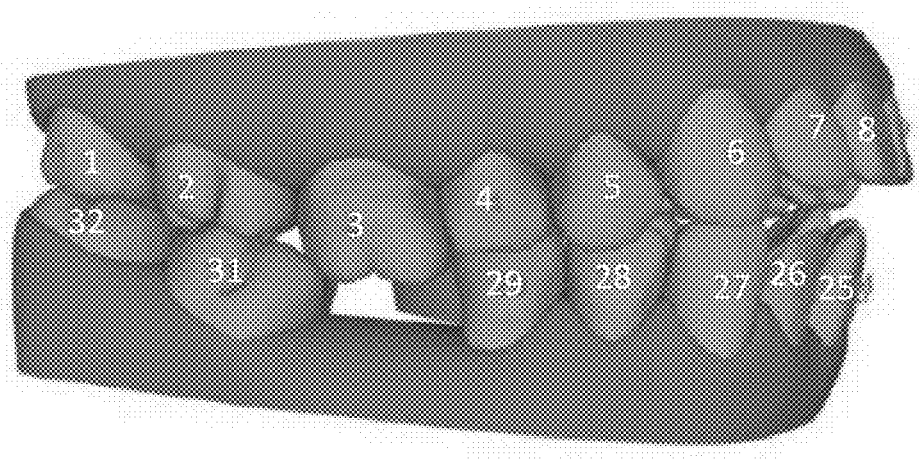

FIG. 1A illustrates teeth numeration from a basic tooth segmentation process without accounting for missing teeth. As can be seen in FIG. 1A, teeth 32 and 31 are improperly numbered as teeth 31 and 30, respectively, due to of missing tooth 30. The improper numbering is a result of numbering the teeth sequentially from the anterior to posterior teeth without accounting for missing teeth. Thus, in FIG. 1A, a simple numbering sequence on the lower jaw may start with incisor 25 and increase sequentially towards the molars. Since tooth 30 (first molar) is missing in FIG. 1A, the simple numbering sequence will improperly number tooth 31 (second molar) as tooth 30, and will improperly number tooth 32 (third molar) as tooth 31. In contrast, FIG. 1B shows teeth 32 and 31 properly numbered. Likewise, the numbering sequence may be improperly numbered if there are supernumerary (extra) teeth or oddly shaped teeth.

The present disclosure presents one or more novel processes and apparatuses for identifying and/or numbering teeth. The methods can provide a fast approach to finding a "global" solution for numbering an entire arch that is robust to both missing teeth and supernumerary teeth. Some implementations herein entail computing the probability that each tooth object corresponds to each possible tooth type, and finding the tooth numbering that maximizes the joint probability distribution of the entire arch. The input may include a probability distribution of the objects in the model identified and numbered by a segmentation process. For example, the data may be in the form of a matrix where the rows (or columns) represent the observed objects and the columns (or rows) represent the possible tooth numbers, with each cell in the matrix corresponding to the probability that a particular object corresponds to a given tooth number. This probability distribution information can be used to find the most probable assignment of tooth objects to tooth numbers. The methods and apparatuses described herein can be separate from, or integrated with, a tooth segmentation method or apparatus.

Figure 2A:
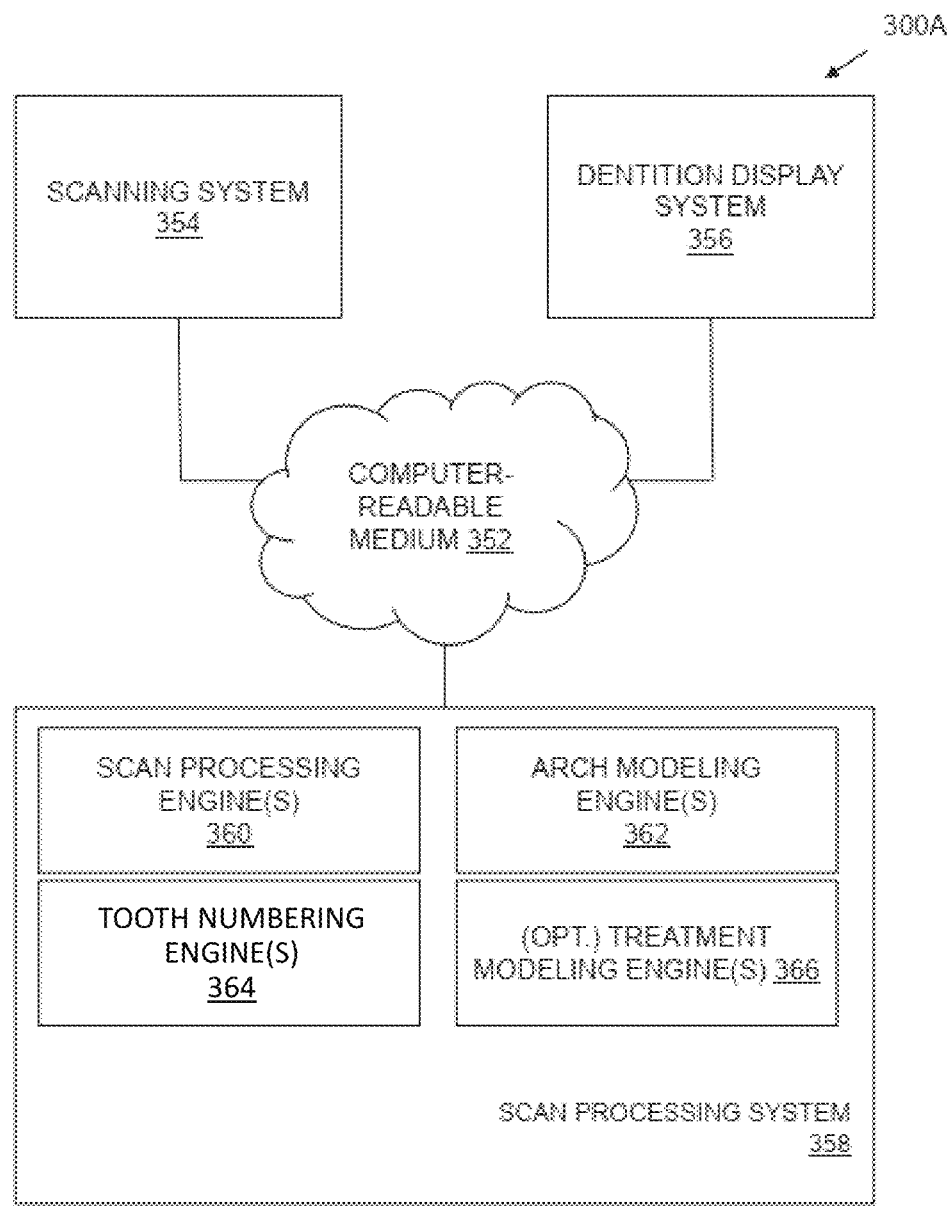
FIG. 2A is a diagram showing an example of a computing environment configured to digitally scan a dental arch with abnormal teeth therein.

FIG. 2A is a diagram showing an example of a computing environment 300A configured to digitally scan a patient's dental arches with missing teeth therein. The environment 300A includes a computer-readable medium 352, a scanning system 354, a dentition display system 356, and a scan processing system 358. One or more of the modules in the computing environment 300A may be coupled to one another or to modules not explicitly shown. The computer-readable medium 352 and other computer readable media discussed in this paper are intended to represent a variety of potentially applicable technologies. For example, the computer-readable medium 352 can be used to form a network or part of a network.

Where two components are co-located on a device, the computer-readable medium 352 can include a bus or other data conduit or plane. Where a first component is co-located on one device and a second component is located on a different device, the computer-readable medium 352 can include a wireless or wired back-end network or LAN. The computer-readable medium 352 can also encompass a relevant portion of a WAN or other network, if applicable.

The scanning system 354 may include a computer system configured to capture still images, video, and/or other media of a patient's dental arches. The scanning system 354 may include memory, one or more processors, and sensors to detect contours on a patient's dental arches. The scanning system 354 may be implemented as a camera, an intraoral scanner, an x-ray device, an infrared device, etc. The scanning system 354 may include a system configured to provide a virtual representation of a mold of patient's dental arches. A "dental arch," as used herein, may include at least a portion of a patient's dentition formed by the patient's maxillary or mandibular teeth, when viewed from an occlusal perspective. A dental arch may include one or more maxillary or mandibular teeth of a patient, such as all teeth on the maxilla or mandible or a patient. One or both dental arches may be included in any of the methods described herein, unless the context make it clear otherwise. The scanning system 354 may be used as part of an orthodontic treatment plan. In some implementations, the scanning system 354 is configured to capture a patient's dental arches at a beginning stage, an intermediate stage, etc. of an orthodontic treatment plan.

The dentition display system 356 may include a computer system configured to display at least a portion of a dentition of a patient. The dentition display system 354 may include memory, one or more processors, and a display device to display the patient's dentition. The dentition display system 356 may be implemented as part of a computer system, a display of a dedicated intraoral scanner, etc. In some implementations, the dentition display system 356 facilitates display of a patient's dentition using scans that are taken at an earlier date and/or at a remote location. It is noted the dentition display system 356 may facilitate display of scans taken contemporaneously and/or locally to it as well. As noted herein, the dentition display system 356 may be configured to display the intended or actual results of an orthodontic treatment plan applied to a dental arch scanned by the scanning system 354. The results may include 3D virtual representations of the dental arches, 2D images or renditions of the dental arches, etc.

The scan processing system 358 may include a computer system configured to process scans of a patient's dentition taken by the scanning system 354. As noted herein, the scan processing system 358 may be configured to process scans of missing teeth in a dental arch. "Missing teeth," as used in this context, may refer to teeth that do not show up in a scan of a dental arch due to a variety of factors. Missing teeth may include teeth that are missing due to various reason (genetics, trauma, removal, etc.), unerupted teeth, etc. The scan processing system 358 may include scan processing engine(s) 360, arch modeling engine(s) 362, tooth numbering engine(s) 364, and optional treatment modeling engine(s) 366. One or more of the modules of the scan processing system 358 may be coupled to each other or to modules not shown.

As used herein, any "engine" may include one or more processors or a portion thereof. A portion of one or more processors can include some portion of hardware less than all of the hardware comprising any given one or more processors, such as a subset of registers, the portion of the processor dedicated to one or more threads of a multi-threaded processor, a time slice during which the processor is wholly or partially dedicated to carrying out part of the engine's functionality, or the like. As such, a first engine and a second engine can have one or more dedicated processors or a first engine and a second engine can share one or more processors with one another or other engines. Depending upon implementation-specific or other considerations, an engine can be centralized or its functionality distributed. An engine can include hardware, firmware, or software embodied in a computer-readable medium for execution by the processor. The processor transforms data into new data using implemented data structures and methods, such as is described with reference to the figures herein.

The engines described herein, or the engines through which the systems and devices described herein can be implemented, can be cloud-based engines. As used herein, a cloud-based engine is an engine that can run applications and/or functionalities using a cloud-based computing system. All or portions of the applications and/or functionalities can be distributed across multiple computing devices, and need not be restricted to only one computing device. In some embodiments, the cloud-based engines can execute functionalities and/or modules that end users access through a web browser or container application without having the functionalities and/or modules installed locally on the end-users' computing devices.

As used herein, "datastores" may include repositories having any applicable organization of data, including tables, comma-separated values (CSV) files, traditional databases (e.g., SQL), or other applicable known or convenient organizational formats. Datastores can be implemented, for example, as software embodied in a physical computer-readable medium on a specific-purpose machine, in firmware, in hardware, in a combination thereof, or in an applicable known or convenient device or system. Datastore-associated components, such as database interfaces, can be considered "part of" a datastore, part of some other system component, or a combination thereof, though the physical location and other characteristics of datastore-associated components is not critical for an understanding of the techniques described herein.

Datastores can include data structures. As used herein, a data structure is associated with a particular way of storing and organizing data in a computer so that it can be used efficiently within a given context. Data structures are generally based on the ability of a computer to fetch and store data at any place in its memory, specified by an address, a bit string that can be itself stored in memory and manipulated by the program. Thus, some data structures are based on computing the addresses of data items with arithmetic operations; while other data structures are based on storing addresses of data items within the structure itself. Many data structures use both principles, sometimes combined in non-trivial ways. The implementation of a data structure usually entails writing a set of procedures that create and manipulate instances of that structure. The datastores, described herein, can be cloud-based datastores. A cloud-based datastore is a datastore that is compatible with cloud-based computing systems and engines.

The scan processing engine(s) 360 may implement one or more automated agents configured to interface with the scanning system 354. The scan processing engine(s) 360 may include graphics engines to gather scans of a dental arch. In some implementations, the scan processing engine(s) 360 format raw data from a scan of a dental arch into a 2D or 3D dental mesh models of the dental arch. The 3D dental mesh models may comprise polyhedral objects that depict teeth and/or other elements of the dental arch in a format that can be rendered on the dentition display system 356. The scan processing engine(s) 360 may provide 3D dental mesh models and/or other data to other modules of the scan processing system 358.

The arch modeling engine(s) 362 may implement one or more automated agents configured to model 2D or 3D dental mesh models into virtual representations of dental arches. In some implementations, the arch modeling engine(s) 362 assign physical and/or geometrical properties to a 2D or 3D dental mesh models that are related to physical/geometrical properties of dental arches. As an example, the arch modeling engine(s) 362 may implement one or more automated segmentation agents that assign tooth identifiers (e.g., universal tooth numbers) to specific portions of a dental mesh model. The arch modeling engine(s) 362 may further evaluate curves and/or other geometric properties of a dental mesh model to determine whether a scan corresponds to a maxilla, a mandible, or other portion of a patient's dentition. The arch modeling engine(s) 362 may be used to determine the number of objects in the model identified as teeth (e.g., as opposed to gingiva) and possible tooth numbers corresponding to the type of tooth (e.g., incisor, canine, molar, primary, permanent, supernumerary, etc.). On a dental scan, a missing tooth may be indicated by two normally non-adjacent teeth being adjacent to each other, and a supernumerary tooth may be indicated by an extra tooth between two normally adjacent teeth.

The tooth numbering engine(s) 364 may be configured to assign a number to each of the objects identified as teeth by the arch modeling engine(s) 362. The tooth numbering engine(s) 364 may take into account object that are not regular teeth, such as incisors, canines, pre-molars and molars. For example, the tooth numbering engine(s) 364 may take into account one or more supernumerary teeth that may be present and/or one or more teeth that may be missing. The tooth numbering engine(s) 364 may be configured to compare characteristics of the objects identified as teeth by the arch modeling engine(s) 362 with characteristics of teeth stored in a database. Results of this analysis can be in the form of a probability distribution, such as a matrix with each cell in the matrix corresponding to a probability that a particular object corresponds to a given tooth number. In various implementations, the tooth numbering engine(s) 364 provide the arch modeling engine(s) 362 and/or other modules instructions to "re-segment," such as re-number the teeth in a scan of a dental arch in order to accommodate missing teeth in that dental arch. An example of the tooth numbering engine(s) 364 is shown as the missing tooth processing engine(s) 364b, in FIG. 2B.

The optional treatment modeling engine(s) 366 may be configured to store orthodontic treatment plans and/or the results of orthodontic treatment plans. The optional treatment modeling engine(s) 366 may provide the results of orthodontic treatment plans on 3D dental mesh model. The optional treatment modeling engine(s) 366 may model the results of application of orthodontic aligners to the patient's dental arch over the course of an orthodontic treatment plan.

Figure 2B:
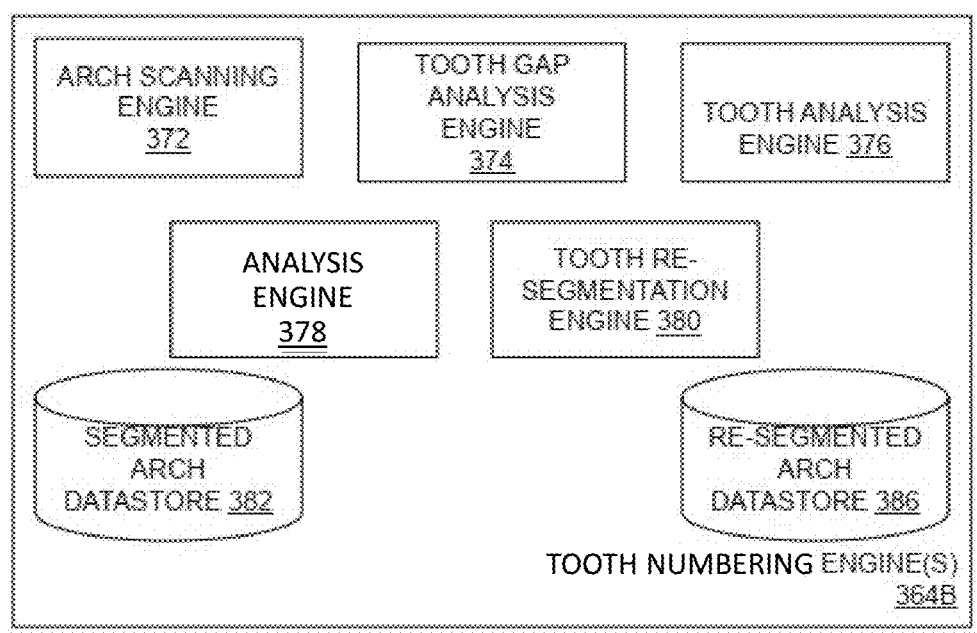
FIG. 2B is a diagram showing an example of missing tooth processing engine(s).

FIG. 2B is a diagram showing an example of the tooth numbering engine(s) 364. The missing tooth processing engine(s) 364 may include one or more of optional an arch scanning engine 372, a tooth gap analysis engine 374, a teeth analysis engine 376, an analysis engine 378, a tooth re-segmentation engine 380, a model arch datastore 382, and a re-segmented arch datastore 386. One or more of the modules of the tooth numbering engine(s) 364 may be coupled to each other or to modules not shown.

The arch scanning engine 372 may implement one or more automated agents configured to scan a dental arch for segmentation data. "Segmentation data," as used herein, may include positions, geometrical properties (contours, etc.), and/or other data that can form the basis of segmenting a dental arch. The arch scanning engine 372 may implement automated agents to number teeth in a dental arch. In some implementations, the arch scanning engine 372 begins numbering teeth at anterior portion (e.g., the midline) of a dental arch and continues numbering through posterior portion(s) of the dental arch. The optional tooth gap analysis engine 374 may determine whether the space between two adjacent teeth in a dental arch meets or exceeds a gap threshold, which may be used to determine whether there is a missing tooth. The tooth analysis engine 376 may implement one or more automated agents configured to determine tooth dimensions in a dental arch. The tooth analysis engine 376 may gather attributes (identifiers, dimensions, etc.) of teeth, e.g., buccal-lingual width and/or mesial-distal width, of adjacent teeth and/or contralateral teeth. The tooth analysis engine 376 may evaluate and/or compare these attributes with attributes of ideal or model teeth in an ideal or model dental arch. The tooth analysis engine 376 may provide other modules (analysis engine 378, the tooth re-segmentation engine 380, etc.) with specific areas of a dental arch that contain teeth that do not match similar teeth in an ideal or model dental arch. The segmented arch datastore 382 may be configured to store segmented data related to dental arches. The model dental arch data may comprise segments numerous dental arches, including tooth identifiers of teeth normally present in a model dental arch. The segmented arch datastore 382 may further store data related to tooth widths of the various tooth types of a plurality of patients, including incisor widths, canine widths, and premolar widths. The analysis engine 378 may be configured to calculate the probability that an object observed in a scan and identified as a tooth should be assigned a particular tooth number. The analysis engine 378 may be informed by one or more of the arch scanning engine 372, tooth gap analysis engine 374, tooth analysis engine 376 and segmented arch datastore 382. The calculation can be done over the full set of identified teeth in an arch, providing a probability distribution of tooth numberings assigned to the objects identified as teeth. In some cases, results from the analysis engine 378 is used to inform the tooth re-segmentation engine 380, and re-segment the dental arch. The re-segmented arch datastore 386 may be configured to store data related to re-segmented dental arches. The re-segmented dental arch data may comprise segments of dental arches having missing teeth; the re-segmented dental arch data may have been stored in the re-segmented arch datastore 386 by the tooth re-segmentation engine 380.

Methods for calculating and numbering the dental arch will now be described.

To formalize the problem, assume that we have a set of ordered observations O and a set of ordered tooth numbers T. We can define Nc=|T| (i.e., the size of the set of tooth numbers) and No=|O| observations of objects in an arch. We can define P as an No by (Nc+1) matrix of probabilities with one row per observation and one column per tooth type. Each cell, Pij, represents a single observation that object i is tooth number j, and the Nc+1$^{th}$ column represents the probability that a given object is a supernumerary tooth.

The desired output of the system is B, a No by (Nc+1) matrix where each Bij∈{0,1} refers to the assignment of observation i to tooth number j, where a value of 0 indicates no assignment and a 1 indicates assignment. Finding this matrix can be treated as a modified version of the standard assignment problem where the goal is to maximize the probability of a solution according to equation (1) below:

$$\overset{*}{B} = \underset{B}{\mathrm{argmax}} \sum_i \sum_j P_{ij} B_{ij} \qquad (1)$$

subject to the following constraints:

$$B_{ij} \in \{0,1\}; \forall i,j \quad (C_1)$$

$$\Sigma_j B_{ij}=1; \forall i \quad (C_2)$$

$$\Sigma_i B_{ij} \leq 1; \forall j \leq N_c \quad (C_3)$$

$$\Sigma_{k=1}^{N_o}\Sigma_{l=i}^j B_{kl} = \Sigma_{k=i}^j \Sigma_{l=j}^{N_c} B_{k,l} = 1; \forall B_{ij}=1 \quad (C_4)$$

Constraint 1 requires the assignments to be binary, i.e., either a part of the solution or not. Constraint 2 ensures that all observations are labeled. Constraint 3 ensures that each label (other than supernumerary) is assigned to only 1 tooth. Constraint 4 ensures that our observations are ordered such that if an assignment Oi=Tj is made, no previous observations can have a larger tooth number; likewise, no later observation can have a smaller tooth number.

Unfortunately, unlike the standard assignment problem which can be solved quickly using well known algorithms (e.g., such as the Kuhn-Munkres algorithm), as stated, this problem is NP-Hard and does not have a polynomial time solution.

Missing and Supernumerary Teeth

With the naive approach, one might have to explicitly identify the set of all matrices, B, which match the problem constraints. Here we recognize that the problem can be conceptually simplified. Imagine that the number of observations, No, was equal to Nc, the number of teeth that we are interested in numbering. Moreover, assume we know that there are no supernumerary teeth, i.e., Ns=0. In this case, the only solution matching the constraints of the naive problem is B=I, where I is the identity matrix of size No X No.

To address the problem of missing or supernumerary teeth, we recognize that supernumerary teeth are a subset of the objects and missing teeth are a subset of the tooth numbers:

$$\mathcal{S} \subset \{1, \ldots, N_o\} \quad (2)$$

$$\mathcal{M} \subset \{1, \ldots, N_c\} \quad (3)$$

Subject to the constraint that No−|S|=Nc−|M|>0. A concrete example is to imagine that we are trying to label 14 objects using 16 permanent teeth numbers. We know that if we have 0 supernumerary teeth, then 2 teeth are missing. Alternatively, we could have 3, 4, or 5 missing teeth if we have 1, 2, or 3 supernumerary teeth present. For any set of hypothesized supernumerary teeth, we can define the number of missing teeth as being $$|\mathcal{M}| = N_c - N_o + |\mathcal{S}| \quad (4)$$

This allows us to think about the problem in a probabilistic framework, where our goal is to find the sets of supernumerary teeth, S*, missing teeth, M*, and the assignment matrix, B*, which maximize the joint posterior probability distribution for the arch:

$$\overset{*}{\mathcal{S}}, \overset{*}{\mathcal{M}}, \overset{*}{B} = \underset{SMB}{\operatorname{argmax}} p(\mathcal{S}, \mathcal{M}, B | P) \quad (5)$$

where $$p(\mathcal{S}, \mathcal{M}, B | P) \propto p(P | \mathcal{S}, \mathcal{M}, B) \times p(\mathcal{S}, \mathcal{M}, B) \quad (6)$$

and $$p(P | \mathcal{S}, \mathcal{M}, B) = \prod_i P_{/SM}(i, i) \times \prod_{s \in S} P(s, N_c + 1) \quad (7)$$

the notation $P_{/SM}$ indicates the matrix constructed by removing the rows in S and the columns in M from the matrix P. We then factor p(S,M,B) as $$p(\mathcal{S}, \mathcal{M}, B) = p(B | \mathcal{S}, \mathcal{M}) p(\mathcal{M} | \mathcal{S}) p(\mathcal{S}) \quad (8)$$

noting: 1) The assignments in B are completely determined by S and M, and therefore p(B|S,M) α 1; 2) For a given number of observations, No, the number of missing teeth is determined based on the number of supernumerary teeth. If we assume that all teeth are equally likely to be missing and that the set of missing teeth is independent of S, then p(M|S)=p(M)α1. Note that these two assumptions can be removed if we have data regarding the prior probability of a given tooth number being missing. For example, a Gap Analysis engine may describe the probability that one or more teeth are missing based on the size of the gap between two adjacent teeth; and 3) Assuming that all observations are a priori equally likely to be supernumerary, then we can treat the prior probability of the set S as the probability of the size of the set S, i.e., p(S)=p(|S|). A reasonable choice for the prior probability of the number of supernumerary teeth is p(|S|)∼Poisson (|S|); $\lambda_s$), where $\lambda_s$ is the per-arch rate of supernumerary teeth (which could be different depending on arch type or underlying population differences in different regions). This also bounds the number of supernumerary teeth by penalizing the assignment of large numbers of observations to supernumerary in a principled manner and reduces the computational complexity of the assignment problem. Thus, in general, the methods and apparatuses described herein (including systems and non-transitory computer-readable memory) may be configured to include the probability of missing teeth as part of a set of probabilities. As mentioned, in some variations the probability of missing teeth may be assumed to be equally likely for each tooth type. Alternatively, in some variations the probability that a tooth in a set of teeth (e.g., in some variations including supernumerary teeth) is missing may be based on determining the set of probabilities includes a probability of missing teeth. This probability may be based on a predetermined and/or preset, non-zero value. In some variations, the probability of missing teeth is based on a gap distance between the teeth.

From the above, we can describe the joint posterior probability of the arch numbering as $$p(\mathcal{S}, \mathcal{M}, B | P) \propto \left[\prod_{i=1}^{N_c - |\mathcal{M}|} P_{/SM}(i, i)\right] \times \left[\prod_{s \in S} P(s, N_c + 1)\right] \times p(\mathcal{M}) \times \frac{\lambda |S|_e - \lambda}{|S|!} \quad (9)$$

Recognizing that $$\overset{*}{\mathcal{S}}, \overset{*}{\mathcal{M}}, \overset{*}{B} = \underset{SMB}{\operatorname{argmax}} \; p(\mathcal{S}, \mathcal{M}, B | P) \quad (10)$$

$$= \underset{SMB}{\operatorname{argmax}} \; \log[p(\mathcal{S}, \mathcal{M}, B | P)]$$

we can rewrite Eq 9 to improve numerical stability and increase computational performance:

$$\log[p(\mathcal{S}, \mathcal{M}, |B|P)] \propto \qquad (11)$$

$$\left[ \prod_{i=1}^{N_c-|\mathcal{M}|} \log P_{/SM}(i, i) \right] +$$

$$\left[ \sum_{s \in S} \log P(s, N_c+1) \right] + \log p(\mathcal{M}) + |\mathcal{S}|\log \lambda - \lambda - \sum_{s=1}^{|\mathcal{S}|} \log s$$

We can now compute all possible sets of missing and supernumerary teeth, where $|M|=Nc-No+|S|$, $S \subset \{1, \ldots, No\}$, and $M \subset \{1, \ldots, Nc\}$. To find the solution to Equation 5 we need to generate every possible set S and set M and evaluate Equation 11. Unfortunately, the number of potential solutions is non-polynomial in the number of missing and supernumerary teeth. If we consider 16 possible teeth, No observations and as many as Ms possible supernumerary, then the number of solutions is:

$$\sum_{s=0}^{M_s} \binom{N_o}{s} \binom{16}{N_o - s} \qquad (12)$$

TABLE 1

Number of solutions for various No and Ms.

| | $M_s$ | | | | |
|---|---|---|---|---|---|
| $N_o$ | 1 | 9 | 3 | 4 | 5 |
| 12 | 54.2K | 583K | 3.10M | 9.47M | 18.5M |
| 13 | 24.2K | 365K | 2.66M | 10.8M | 27.4M |
| 14 | 7.96K | 174K | 1.76M | 9.78M | 32.7M |
| 15 | 1.82K | 60.6K | 889K | 6.85M | 30.9M |
| 16 | 257 | 14.7K | 328K | 3.64M | 22.7M |

As seen in Table 1, to consider even small numbers of potentially supernumerary teeth, we need to evaluate Equation 11 tens of thousands to tens of millions of times. Fortunately, the problem is amenable to a tree-based solution that allows for bad assignments to be pruned early in the process.

Tree-Based Solution

Combinatorial problems, including the selection of subsets of size k from a set of n objects (n choose k or nCk), can be implemented using recursion to walk a tree structure of depth k. The tree is constructed such that the root node contains the empty set and its child nodes each contain a set with a single element which is one possible "first" element of the set. Each set of child nodes adds an additional element to the set, constrained in such a way that at the k-th level, all possible sets of nCk are enumerated in the leaf nodes.

In this work, we construct a set of multitrees (one multitree per hypothesized number of supernumerary teeth). The first level of the multitree is a tree that identifies sets of supernumerary teeth at each of its leaf nodes. From each of these leaf nodes, we then construct a new tree whose leaf nodes contain all possible missing teeth, subject to the previously defined problem constraints.

For any hypothesized number of supernumerary teeth, |S|, in a set of objects of size |O|, we can construct a first-level tree where each leaf node is a possible subset of the supernumerary teeth in the set of observations. Each leaf of the supernumerary tree is then the root node of a missing tooth tree (or second level tree) in which we select Nc−|O|+ |S|=|M| missing teeth from the set of tooth labels (e.g., 1 to 16). The leaf nodes of the missing teeth trees are then all combinations of sets S and M where |S| is the hypothesized size.

By enumerating over all possible hypotheses for the size of |S| (from 0 to |O|), we can enumerate all possible solutions for S and M given a set of observations, O. Unfortunately, this is just a tree-based implementation to the problem in the previous section, and still consists of a very large number of possible solutions, where each solution requires the evaluation of the log likelihood function (Eq 11) in order to find the solution with the maximum likelihood. To shorten this search, we recognize that the number of solutions of |O| choose |S| is equivalent to the number of solutions in |O| choose |O|−|S|, in other words, finding the set of observations that are not supernumerary, S, is computationally equivalent to finding the set of observations that are supernumerary. Likewise, finding the set of teeth that are not missing, M, is computationally equivalent to finding the set of teeth that are missing.

Using this observation, we now build a multitree which identifies the sets of not-supernumerary teeth and not missing teeth at its leaves. Because we add a not supernumerary or not-missing tooth at each level of the tree, we can create a partial log likelihood at each node of the tree by adding by the relevant assignment log probability corresponding to that interior node to the node's parent's partial log likelihood. By the time we reach a leaf node in the multitree, we have evaluated Eq 11 for the particular solution represented in that leaf node.

This partial log likelihood computation has two important properties:

1. It significantly reduces the number of operations required to evaluate the solutions, because only the necessary portions of the calculation are performed at each node. We do not duplicate calculations at the leaf nodes.

2. As the probabilities involved are multinomials, the maximum probability for any given assignment is less than or equal to 1, i.e., the log likelihood will be less than or equal to 0. Therefore, the upper bound of any child node's partial log likelihood is the partial log likelihood of its parent, i.e., the child node cannot be more likely than its parent.

This second property allows for the pruning of the search space. By proceeding with depth first search down the multitree and tracking the current maximum log likelihood of all visited solutions, we can prune branches of the tree when we find that an intermediate node has a log likelihood which is less than that of the current best solution.

This form of solution also provides us with a natural method for determining which hypotheses for the number of supernumerary teeth should be explored. We can ignore solutions where the prior log probability of the size of S, |S|, is less than the current best maximum log likelihood solution.

Using this pruning approach, we find that we explore significantly less of the solution space than a non-pruning approach. Moreover, the log likelihoods of the solutions are generated during the depth first search, eliminating the need to perform a complete evaluation of Eq 11 at each leaf node.

One example of a method for the tree-based maximum likelihood solver can be seen in FIG. 5, showing one implementation of the methods described herein. The inputs are the matrix P with the probabilities for No observations assigned to Nc+1 tooth numbers (including supernumerary) and the parameterization of the prior distribution for the number of supernumerary teeth, $\lambda_s$. The results are stored in Best S and Best M. Best S will contain the list of objects which are not supernumerary. Best M will contain the assignments from those objects to a particular tooth type. Note that in FIG. 5, all arrays and matrices are indexed from 0, including the object and tooth numbers in Best S and Best M. The method shown in FIG. 5 is just one example, and other implementations are possible, including variations in which the probability of missing teeth is included, as mentioned above. For example, in FIG. 5, line 40 of the method may include a probability of missing teeth, which may be added as a term (e.g., included with the LogLikelihood term).

TABLE 2

Performance results for simulating 1,000 iterations of the global tooth numbering system for varying values of added error, σ.

| σ | correct | accuracy | tree coverage |
|---|---------|----------|---------------|
| 0.05 | 998 | 0.9970 ± 0.0017 | 0.000074 |
| 0.10 | 992 | 0.9910 ± 0.0030 | 0.000241 |
| 0.15 | 994 | 0.9930 ± 0.0026 | 0.000636 |
| 0.20 | 988 | 0.9870 ± 0.0036 | 0.001226 |
| 0.25 | 982 | 0.9810 ± 0.0043 | 0.002266 |
| 0.30 | 982 | 0.9810 ± 0.0043 | 0.003514 |
| 0.35 | 972 | 0.9711 ± 0.0053 | 0.005222 |
| 0.40 | 966 | 0.9651 ± 0.0058 | 0.007450 |
| 0.45 | 934 | 0.9331 ± 0.0079 | 0.009777 |
| 0.50 | 915 | 0.9142 ± 0.0088 | 0.012156 | following logic:

$N_c = 16$ $\lambda s = 0.25$ $\lambda_m = 2.5$ $|\mathcal{S}| \sim \text{Poisson}(\lambda_s)$ $|\mathcal{M}| \sim \text{Poisson}(\lambda_m)$ $|\mathcal{O}| = N_c + |\mathcal{S}| - |\mathcal{M}|$ $\mathcal{M} \sim \text{Choose}(N_c, |\mathcal{M}|)$ $\mathcal{S} \sim \text{Choose}(|\mathcal{O}|, |\mathcal{S}|)$ $\lambda_s$ and $\lambda_m$ are the rates at which we observe supernumerary and missing teeth, respectively. The size of the sets of these teeth are then drawn from a Poisson distribution at the given rate. From Eq 4 we can then determine the number of observations in this simulation. Knowing S, M and |O|, we can generate a ground truth matrix, Y, having a 1 at each assignment from observation to tooth type and a 0 at all other locations. For a specific run of the simulation, we generate an observed probability matrix, P, using the half-normal distribution to generate noise:

$N = |\mathcal{N}(0,\sigma)|$ $\dot{P} = Y + N$ $P = Row\ \text{Normalization}(\dot{P})$;

where σ is a varying amount of noise or error in our probability measurements. We vary σ from 0.05 to 0.5 and for each value of σ run 1,000 simulations, noting the number of correct answers, the accuracy (modeling the simulations as a set of Bernoulli trials having an uninformative Beta prior) and the average fraction of the solution space that was explored.

As can be seen in Table 2, increasing the noise in the observations unsurprisingly results in reduced performance.

Figure 3:
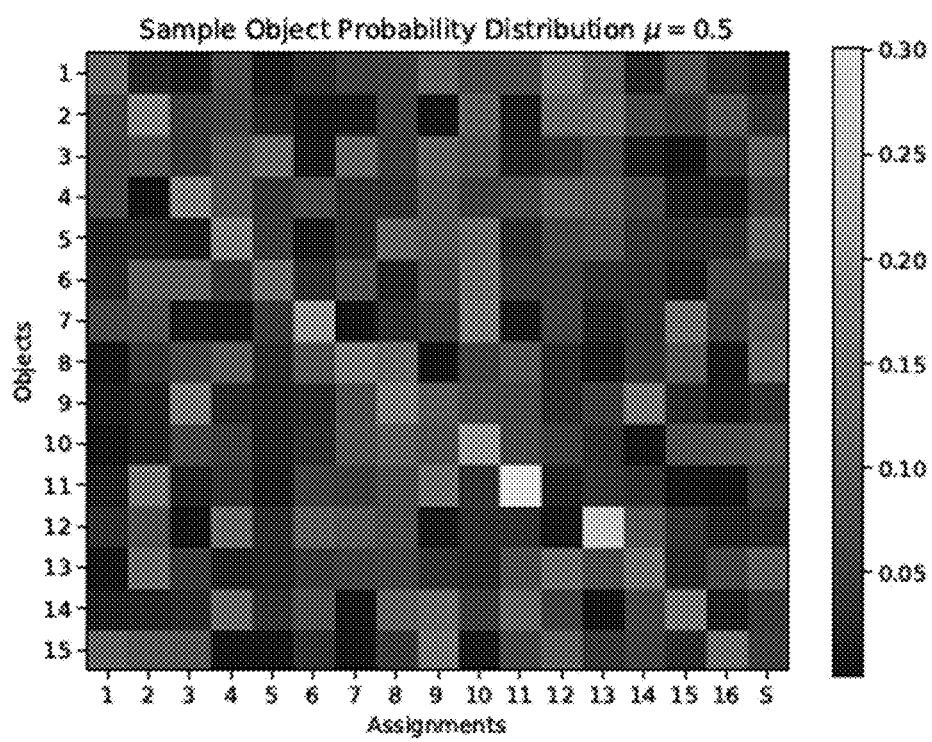
FIG. 3 is an example of a sample probability matrix P for a $\sigma=0.50$ simulation with two missing teeth (9 and 12) and one supernumerary object (3).

FIG. 3 shows a sample probability matrix, P, from the σ=0.50 simulation with two missing teeth (9 and 12) and one supernumerary object (3). It is also interesting to note that increasing observation noise requires a search of larger portions of the tree. However, even for the case of σ=0.50, only 1.2% of the entire solution space must be explored in order to find the maximum likelihood solution, resulting in a solution that can be found in milliseconds. Consider the sample from the σ=0.50 simulation shown in FIG. 1. In this sample, no probability mapping an object to a tooth number is greater than 0.3. There are two missing teeth (9 and 12) and one of the objects is supernumerary (object 3). Moreover, for several teeth numbers (5, 14, and supernumerary) the maximum probability for the column is not the correct assignment. The maximum-likelihood solver is still able to select the correct assignment of all teeth, including the supernumerary tooth, while visiting only 2% of the solution space.

Previous solutions to the tooth numbering problem have focused on identifying the central incisors and working distally. These solutions typically require manual intervention to identify missing teeth numbers, are prone to error, and have no mechanism to correct for mistakes made in the initial assignments. In contrast, the maximum likelihood solution makes globally optimal assignments of observations, allowing for both supernumerary objects and missing teeth.

The maximum likelihood solver does require a set of input probabilities. These probabilities will be domain based. For example, in previous work, our group has developed 3D features (e.g., (i) PCA components of a structured point representation, (ii) rotation invariant spherical harmonic representations, or (iii) 3D graph and voxel-based convolutional neural networks) that could be used to categorize teeth-like objects into the probability that they are of a particular dental type. Such a system would be similar to the system used to identify primary teeth in the Invisalign First, Phase 1 product. We anticipate that computing these probabilities should add minimal overhead to the overall assignment problem and that the requirements for perfect classification are mitigated by the global nature of the maximum likelihood solution.

Figure 3A:
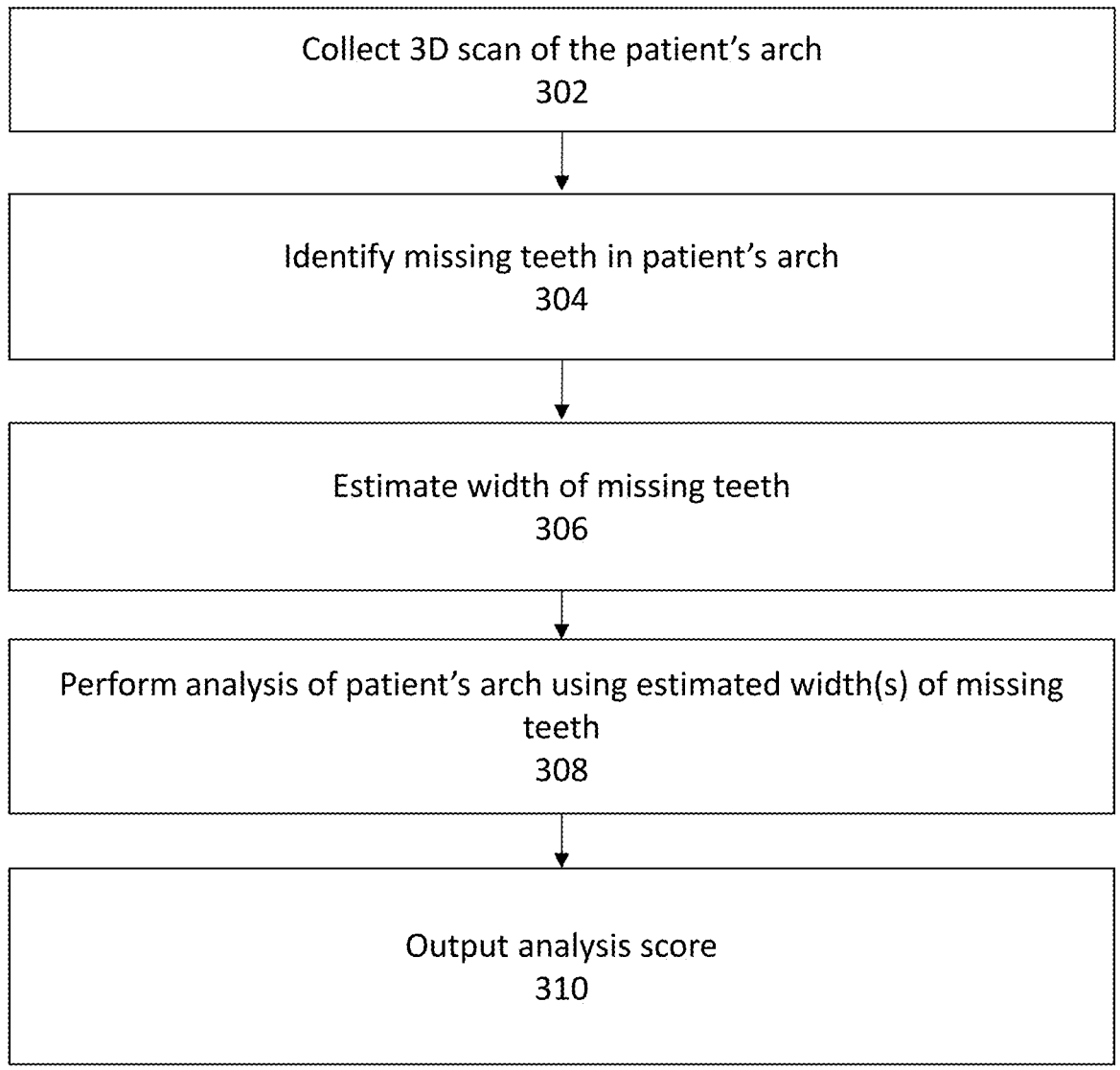
FIG. 3A is an example of a method for numbering (via a standardized numbering system) identified tooth objects forma digital model of a patient's teeth.
Figure 4:
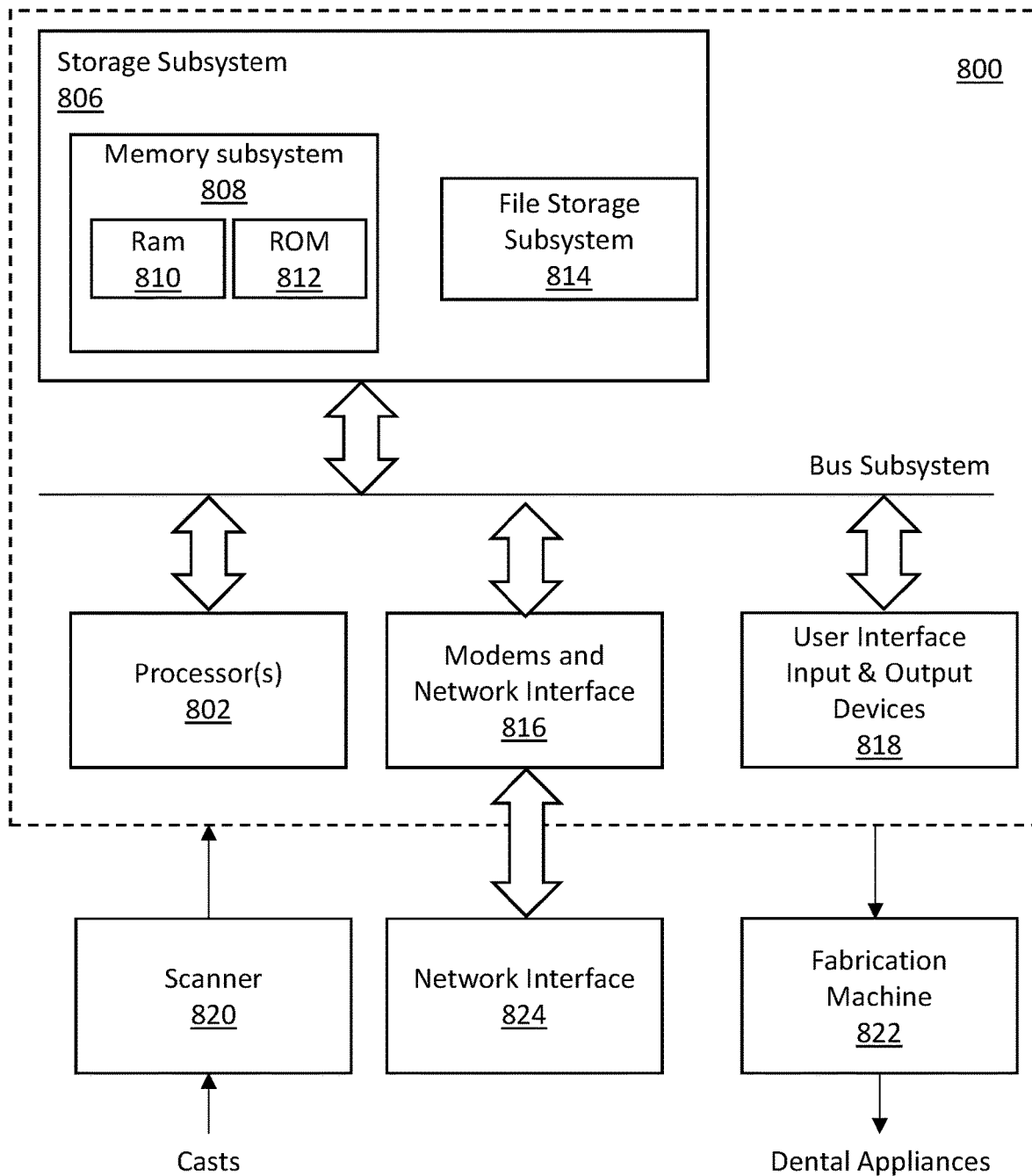
FIG. 4 is a simplified block diagram showing an example of a data processing system for designing and manufacturing an orthodontic aligner.

FIG. 3A illustrates a flowchart 400 that describes a tooth numbering process for numbering teeth in accordance with some embodiments. FIG. 4 illustrates one example of a method (described here as encoded instructions) for performing a tree-based maximum likelihood solver.

The methods described herein may be performed by an apparatus, such as a data processing system, which may include hardware, software, and/or firmware for performing many of these steps described above. For example, FIG. 4 is a simplified block diagram of a data processing system 800. Data processing system 800 typically includes at least one processor 802 which communicates with a number of peripheral devices over bus subsystem 804. These peripheral devices typically include a storage subsystem 806 (memory subsystem 808 and file storage subsystem 814), a set of user interface input and output devices 818, and an interface to outside networks 816, including the public switched telephone network. This interface is shown schematically as "Modems and Network Interface" block 816, and is coupled to corresponding interface devices in other data processing systems over communication network interface 824. Data processing system 800 may include a terminal or a low-end personal computer or a high-end personal computer, workstation or mainframe.

The user interface input devices typically include a keyboard and may further include a pointing device and a scanner. The pointing device may be an indirect pointing device such as a mouse, trackball, touchpad, or graphics tablet, or a direct pointing device such as a touchscreen incorporated into the display. Other types of user interface input devices, such as voice recognition systems, may be used.

User interface output devices may include a printer and a display subsystem, which includes a display controller and a display device coupled to the controller. The display device may be a cathode ray tube (CRT), a flat-panel device such as a liquid crystal display (LCD), or a projection device. The display subsystem may also provide nonvisual display such as audio output.

Storage subsystem 806 maintains the basic programming and data constructs that provide the functionality of the present invention. The software modules discussed above are typically stored in storage subsystem 806. Storage subsystem 806 typically comprises memory subsystem 808 and file storage subsystem 814.

Memory subsystem 808 typically includes a number of memories including a main random access memory (RAM) 810 for storage of instructions and data during program execution and a read only memory (ROM) 812 in which fixed instructions are stored. In the case of Macintosh-compatible personal computers the ROM would include portions of the operating system; in the case of IBM-compatible personal computers, this would include the BIOS (basic input/output system).

File storage subsystem 814 provides persistent (nonvolatile) storage for program and data files, and typically includes at least one hard disk drive and at least one floppy disk drive (with associated removable media). There may also be other devices such as a CD-ROM drive and optical drives (all with their associated removable media). Additionally, the system may include drives of the type with removable media cartridges. The removable media cartridges may, for example be hard disk cartridges, such as those marketed by Syquest and others, and flexible disk cartridges, such as those marketed by Iomega. One or more of the drives may be located at a remote location, such as in a server on a local area network or at a site on the Internet's World Wide Web.

In this context, the term "bus subsystem" is used generically so as to include any mechanism for letting the various components and subsystems communicate with each other as intended. With the exception of the input devices and the display, the other components need not be at the same physical location. Thus, for example, portions of the file storage system could be connected over various local-area or wide-area network media, including telephone lines. Similarly, the input devices and display need not be at the same location as the processor, although it is anticipated that the present invention will most often be implemented in the context of PCS and workstations.

Bus subsystem 804 is shown schematically as a single bus, but a typical system has a number of buses such as a local bus and one or more expansion buses (e.g., ADB, SCSI, ISA, EISA, MCA, NuBus, or PCI), as well as serial and parallel ports. Network connections are usually established through a device such as a network adapter on one of these expansion buses or a modem on a serial port. The client computer may be a desktop system or a portable system.

Scanner 820 is responsible for scanning casts of the patient's teeth obtained either from the patient or from an orthodontist and providing the scanned digital data set information to data processing system 800 for further processing. In a distributed environment, scanner 820 may be located at a remote location and communicate scanned digital data set information to data processing system 800 over network interface 824.

Fabrication machine 822 fabricates dental appliances based on intermediate and final data set information received from data processing system 800. In a distributed environment, fabrication machine 822 may be located at a remote location and receive data set information from data processing system 800 over network interface 824.

The dental appliance fabricated by the fabrication machine 822 can be designed to implement at least a portion of a treatment plan, comprising a shell having a plurality of cavities therein designed to receive teeth of a jaw.

In another embodiment, the system 800 of FIG. 14 can include a non-transitory computing device readable medium having instructions stored thereon that are executable by a processor to cause a computing device to receive, via a computing device, data representing a plurality of teeth and generate a series of incremental tooth arrangements to define a proposed orthodontic treatment.

Various alternatives, modifications, and equivalents may be used in lieu of the above components. Although the final position of the teeth may be determined using computer-aided techniques, a user may move the teeth into their final positions by independently manipulating one or more teeth while satisfying the constraints of the prescription.

Additionally, the techniques described here may be implemented in hardware or software, or a combination of the two. The techniques may be implemented in computer programs executing on programmable computers that each includes a processor, a storage medium readable by the processor (including volatile and nonvolatile memory and/or storage elements), and suitable input and output devices. Program code is applied to data entered using an input device to perform the functions described and to generate output information. The output information is applied to one or more output devices.

Each program can be implemented in a high level procedural or object-oriented programming language to operate in conjunction with a computer system. However, the programs can be implemented in assembly or machine language, if desired. In any case, the language may be a compiled or interpreted language.

Each such computer program can be stored on a storage medium or device (e.g., CD-ROM, hard disk or magnetic diskette) that is readable by a general or special purpose programmable computer for configuring and operating the computer when the storage medium or device is read by the computer to perform the procedures described. The system also may be implemented as a computer-readable storage medium, configured with a computer program, where the storage medium so configured causes a computer to operate in a specific and predefined manner.

While preferred embodiments of the present disclosure have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. Numerous different combinations of embodiments described herein are possible, and such combinations are considered part of the present disclosure. In addition, all features discussed in connection with any one embodiment herein can be readily adapted for use in other embodiments herein. It is intended that the following claims define the scope of the invention and that methods and structures within the scope of these claims and their equivalents be covered thereby.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others.

Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A computer-implemented method for accurately assigning tooth numbering to teeth of a patient's dental arch, the method comprising:
   receiving or identifying tooth objects from a digital model of the patient's dental arch;
   determining a set of probabilities including, for each received or identified tooth object from the digital model of the patient's dental arch, a probability that the received or identified tooth object corresponds to each possible tooth type, wherein each possible tooth type includes a set of known teeth types and one or more supernumerary teeth; and
   assigning a tooth numbering to each tooth object from the digital model of the patient's dental arch based on determining a maximum joint probability over a distribution of each possible tooth type for each of the received or identified tooth objects using the set of probabilities.

2. The method of claim 1, wherein determining the set of probabilities includes a probability of missing teeth.

3. The method of claim 2, wherein the probability of missing teeth is assumed to be equally likely for each tooth type.

4. The method of claim 2, wherein the probability of missing teeth is based on one or more of: a gap distance between the teeth of the patient's dental arch, and predetermined value based on tooth type.

5. The method of claim 1, wherein receiving or identifying tooth objects comprises identifying tooth objects from the digital model of the patient's dental arch by segmenting the digital model of the patient's dental arch.

6. The method of claim 1, wherein receiving or identifying tooth objects comprises receiving the digital model of the patient's dental arch with tooth objects which have been identified.

7. The method of claim 1, wherein determining a maximum joint probability over a distribution of each possible tooth type for each of the received or identified tooth objects comprises traversing a branched multitree structure having one tree for each of the one or more supernumerary teeth, wherein each of a node of each tree is a subset of possible tooth numbering assignments for the received or identified tooth objects.

8. The method of claim 7, wherein each tree is traversed by starting with an initial best joint probability and eliminating branches of the tree having a lower joint probability than a current best joint probability, wherein the current best joint probability is adjusted from the current best joint probability when a leaf node of the tree has a higher joint probability.

9. The method of claim 1, wherein the known teeth types are represented using one or more of: Universal Numbering System (1-32), Palmer Notation, and ISO 3950 FDI World Dental Federation notation.

10. The method of claim 1, wherein each possible tooth type includes a set of known teeth types and at least two supernumerary teeth.

11. The method of claim 1, wherein the tooth objects are missing at least one tooth object corresponding to a standard tooth number.

12. The method of claim 1, further comprising creating an orthodontic treatment plan to reposition at least one tooth of the patient using the assigned tooth numbering.

13. The method of claim 1, wherein determining the set of probabilities comprises determining an initial set of probabilities using a principal component analysis or spherical harmonics analysis.

14. A computer-implemented method for accurately assigning tooth numbering to teeth of a patient's dental arch, the method comprising:
   receiving or identifying tooth objects from a digital model of the patient's dental arch;
   determining a set of probabilities including, for each received or identified tooth object from the digital model of the patient's dental arch, a probability that the tooth object corresponds to each possible tooth type, wherein each possible tooth type includes a set of known teeth types and one or more supernumerary teeth;
   determining a joint probability for each possible assignment of the received or identified tooth objects by using the set of probabilities and traversing one or more branched structures having nodes between each branch of the one or more branched structure wherein each node is a possible tooth numbering assignment for the received or identified tooth objects; and
   assigning a tooth numbering to each tooth object from the digital model of the patient's dental arch based on finding the assignment in a leaf node of a tree with a maximum probability over a distribution of all possible tooth number assignments for each of the received or identified tooth objects.

15. A system comprising:
   one or more processors;
   memory coupled to the one or more processors, the memory storing computer-program instructions, that, when executed by the one or more processors, perform a computer-implemented method comprising:
   receiving or identifying tooth objects from a digital model of a patient's dental arch;
   determining a set of probabilities including, for each received or identified tooth object from the digital model of the patient's dental arch, a probability that the received or identified tooth object corresponds to each possible tooth type, wherein each possible tooth type includes a set of known teeth types and one or more supernumerary teeth; and assigning a tooth numbering to each received or identified tooth object from the digital model of the patient's dental arch based on determining a maximum joint probability over a distribution of each possible tooth type for each of the received or identified tooth objects using the set of probabilities.

16. The system of claim 15, wherein determining the set of probabilities includes a probability of missing teeth.

17. The system of claim 16, wherein the probability of missing teeth is assumed to be equally likely for each tooth type.

18. The system of claim 16, wherein the probability of missing teeth is based on one or more of: a gap distance between the teeth of the patient's dental arch, and predetermined value based on tooth type.

19. The system of claim 15, wherein receiving or identifying tooth objects comprises identifying tooth objects from the digital model of the patient's dental arch by segmenting the digital model of the patient's dental arch.

20. The system of claim 15, wherein receiving or identifying tooth objects comprises receiving the digital model of the patient's dental arch with tooth objects that have been identified.

21. The system of claim 15, wherein determining a maximum joint probability distribution for each of the received or identified tooth objects comprises traversing a branched multitree structure having one tree for each of the one or more supernumerary teeth, wherein each of a node of each tree is a subset of possible tooth numbering assignments for the received or identified tooth objects.

22. The system of claim 21, wherein each tree is traversed by starting with an initial joint probability distribution and eliminating branches of nodes having a lower joint probability than a current joint probability distribution, wherein the current joint probability distribution is adjusted from the initial joint probability distribution when a current node has a higher joint probability.

23. The system of claim 15, wherein the known teeth types are represented using one or more of: Universal Numbering System (1-32), Palmer Notation, and ISO 3950 FDI World Dental Federation notation.

24. The system of claim 15, wherein each possible tooth type includes a set of known teeth types and zero or more supernumerary teeth.

25. The system of claim 15, further comprising creating an orthodontic treatment plan to reposition at least one tooth of the patient using the assigned tooth numbering.

26. The system of claim 15, wherein determining the set of probabilities comprises determining an initial set of probabilities using a principal component analysis or spherical harmonics analysis.

27. A non-transitory computer-readable medium including contents that are configured to cause one or more processors to perform a method comprising:
receiving or identifying tooth objects from a digital model of a patient's dental arch;
determining a set of probabilities including, for each identified received or identified tooth object from the digital model of the patient's dental arch, a probability that the tooth object corresponds to each possible tooth type, wherein each possible tooth type includes a set of known teeth types and one or more supernumerary teeth; and
assigning a tooth numbering to each tooth object from the digital model of the patient's dental arch based on determining a maximum joint probability over a distribution of each possible tooth type for each of the received or identified tooth objects using the set of probabilities.

* * * * *